United States Patent
Takahira et al.

(10) Patent No.: US 8,030,087 B2
(45) Date of Patent: Oct. 4, 2011

(54) METHOD FOR ANALYZING CONCENTRATION OF GLUE CONTAINED IN ELECTROLYTE SOLUTION

(75) Inventors: Masayuki Takahira, Tamano (JP); Yozo Ishihara, Tamano (JP); Ikunobu Sumida, Tamano (JP)

(73) Assignee: Pan Pacific Copper Co., Ltd., Tokyo (JP)

( * ) Notice: Subject to any disclaimer, the term of this patent is extended or adjusted under 35 U.S.C. 154(b) by 102 days.

(21) Appl. No.: 12/216,066

(22) Filed: Jun. 27, 2008

(65) Prior Publication Data

US 2009/0071233 A1    Mar. 19, 2009

(30) Foreign Application Priority Data

Sep. 13, 2007   (JP) ................................. 2007-237836

(51) Int. Cl.
*G01N 30/02*    (2006.01)
(52) U.S. Cl. ........................................ 436/161; 73/61.52
(58) Field of Classification Search .................. 436/161; 73/61.52
See application file for complete search history.

(56) References Cited

U.S. PATENT DOCUMENTS

| | | | | |
|---|---|---|---|---|
| 3,655,958 A | * | 4/1972 | West ................................ | 702/23 |
| 4,118,347 A | * | 10/1978 | Ishiguro et al. .................. | 521/53 |
| 4,725,646 A | * | 2/1988 | Kobashi et al. ................... | 525/61 |
| 5,739,014 A | * | 4/1998 | Nakanishi et al. ............... | 435/101 |
| 6,668,624 B2 | * | 12/2003 | Tani et al. ........................ | 73/61.52 |
| 2002/0134142 A1 | | 9/2002 | Tani et al. | |
| 2002/0162386 A1 | * | 11/2002 | Taguchi et al. ............... | 73/61.52 |

FOREIGN PATENT DOCUMENTS

| | | |
|---|---|---|
| CN | 1366613 A | 8/2002 |
| JP | 09-306504 | 11/1997 |
| JP | 2001-337081 A | 12/2001 |
| JP | 2002-296260 A | 10/2002 |
| JP | 2004-169083 | 6/2004 |
| WO | WO 01/92869 A1 | 12/2001 |

OTHER PUBLICATIONS

Japanese Office Action issued in corresponding Japanese Application No. 2007-237836 on Jan. 12, 2010.
Kurihara et al., "Analysis of Glue in Copper Electrolyte Solutions by Column-Switching HPLC", Surface Technology, vol. 53, No. 9 (Sep. 1, 2002) pp. 600-605.
Encyclopaedia Chimica No. 5, NSPA, 1963, pp. 30-31.
Shakulashvili, N., et al. "Separation of Catecholamines and Serotonin by Micellar Electrokinetic Chromatopraphy with UV Detection", Chromatographia, vol. 47, 1/2, Jan. 1998, pp. 89-93.

* cited by examiner

*Primary Examiner* — Michael A Marcheschi
*Assistant Examiner* — Jonathan M Hurst
(74) *Attorney, Agent, or Firm* — Birch, Stewart, Kolasch & Birch, LLP

(57) ABSTRACT

The purpose of the present invention is to provide a method to more easily analyze the concentration of glue in an electrolyte solution, while suppressing the degradation of glue during the analysis. There is provided a method for analyzing the concentration of glue contained in an electrolyte solution containing the electrolyte components by using high performance liquid chromatography, where said method comprises a step wherein an electrolyte solution is added into the eluent pH of which has been adjusted equal to or less than 5 by adding acid to an aqueous solution of phosphate of alkaline metal or alkaline earth metal, a step wherein the eluent into which the electrolyte solution has been added is passed through a separation column the exclusion limit molecular weight of which is 4000-6000 for separating the glue and electrolyte components, and a step wherein the separated glue is detected by a detector.

5 Claims, 3 Drawing Sheets

METHOD FOR ANALYZING CONCENTRATION OF GLUE CONTAINED IN ELECTROLYTE SOLUTION

TECHNICAL FIELD OF THE INVENTION

The present invention relates to a method for analyzing the concentration of gule present in a small amount in an electrolyte solution. Particularly it relates to a method for analyzing the concentration of glue present in a small amount in a copper electrolyte solution.

BACKGROUND OF THE INVENTION

A minute amount of glue (also called as "gelatin") is frequently added into an electrolyte solution used in a method for production of an electrolytic copper by electrolytic smelting, a method for production of a foil of electrolytic copper, and the like. Glue is added for effecting a role of controlling an appearance, mechanical strength, surface crystal structure, physical properties such as roughness of the electrolytic copper and foil of electrolytic copper. It is important for producing a product having a stable quality to control the concentration of glue in the electrolyte solution. Particularly, in the field of the electrolytic smelting of copper, while a method called as a permanent cathode method (PC method) is becoming a major method in which a stainless steel plate is used as a cathode plate onto surface of which copper is electrolytically deposited, it is required to strictly control the concentration of glue when electrolytic copper is produced using the PC method, and therefore, management of the concentration of glue may become more important.

However, the concentration of glue in an electrolyte solution is low, which is in the order of ppm (or mg/L), and therefore its quantitative analysis has been difficult. Further, glue is liable to be degraded by sulfuric acid of high concentration included in the electrolyte solution into low molecular weight substances. Thus, when a long time is required for the analysis, the degradation of glue proceeds during the analysis and an analytical result does not accurately reflect the actual concentration of glue included in the electrolyte solution.

Thus, various types of technologies for analyzing the concentration of glue contained in the electrolyte solution in a minute amount have been proposed. For example, Japanese Patent Application Unexamined Publication No. 2001-337081 discloses an analytical means using high performance liquid chromatography. Concretely, it discloses a method for determining the concentration of glue or gelatin or a distribution of molecular weight thereof comprising the steps of separating glue in an electrolyte solution and an electrolyte component by using a column charged with a filler in the size exclusion mode as a column for high performance liquid chromatography for separating, introducing the glue-containing fluid from which said electrolyte component have been separated into another column charged with a filler in the size exclusion mode, separating the glue according to the molecular weights or distribution of molecular weights, and then introducing the fluid containing the separated glue into a detector.

According to the method described in this document, not only the concentration but also the molecular weight can be analyzed. Therefore, it is a useful method for analyzing a minute amount of glue contained in an electrolyte solution. However, in order to perform an analysis of concentration of glue according to the method, connecting two separation columns in tandem, equipping both of the former and latter columns with a detector, and changing the flow of the fluid timely with a six-way changing valve and the like are required, which makes the analysis system complex. Further, since it is necessary for glue to pass through the two columns, there is a concern that the degradation of glue may occur during the passing.

Further, while this document describes the use of a mixture of sulfuric acid and acetonitrile as a mobile phase, acetonitrile necessitates the trouble for treating waste organic solution.

SUMMARY OF THE INVENTION

Therefore, the problem to be solved by the present invention is to provide a method which makes it possible to analyze more easily the concentration of glue in an electrolyte solution, while suppressing the degradation of glue during the analysis.

The inventors of the present application have studied eagerly for solving said problem, and then, found that said problem might be solved by using high performance liquid chromatography in which a particular mobile phase (eluent) and a particular stationary phase (column) are used.

Therefore, in one aspect, the present invention provides a method for analyzing the concentration of glue contained in an electrolyte solution containing an electrolyte component by using high performance liquid chromatography, comprising the steps of: injecting the electrolyte solution into an eluent whose pH has been adjusted to equal to or less than 5 by adding an acid to an aqueous solution of phosphate of alkaline metal or alkaline earth metal; passing the electrolyte solution-injected eluent through a separation column having an exclusion limit molecular weight of 4000-6000 to separate the glue and the electrolyte component; and detecting the separated glue by a detector.

In one embodiment of the method for analyzing the concentration of glue according to the present invention, pH of the eluent is 2-4.

In another embodiment of the method for analyzing the concentration of glue according to the present invention, the eluent is a mixed aqueous solution of sodium dihydrogenphosphate and phosphoric acid.

In yet another embodiment of the method for analyzing the concentration of glue according to the present invention, the electrolyte solution is diluted 1 to 5 fold with water before injected into the eluent.

In yet another embodiment of the method for analyzing the concentration of glue according to the present invention, after the dilution, the electrolyte solution is kept at 0-30° C., and then injected into the eluent in the state where said temperature condition is satisfied.

In yet another embodiment of the method for analyzing the concentration of glue according to the present invention, the separation column contains a filler composed of a porous hydrophilic vinyl polymer.

In yet another embodiment of the method for analyzing the concentration of glue according to the present invention, the glue is detected by an absorption spectrophotometer, and the concentration of glue is determined by a standard addition method.

According to the present invention, since the analysis system becomes simplified (e.g. only one separation column is required), the analytical operation may become easier and possibility of the degradation of glue during the analysis may be reduced. Further, preparation of the eluent and treatment of the waste liquid may become easier since use of organic substances such as acetonitrile is not required.

PREFERRED EMBODIMENT OF THE INVENTION

Principle of Analysis

Figure 1:
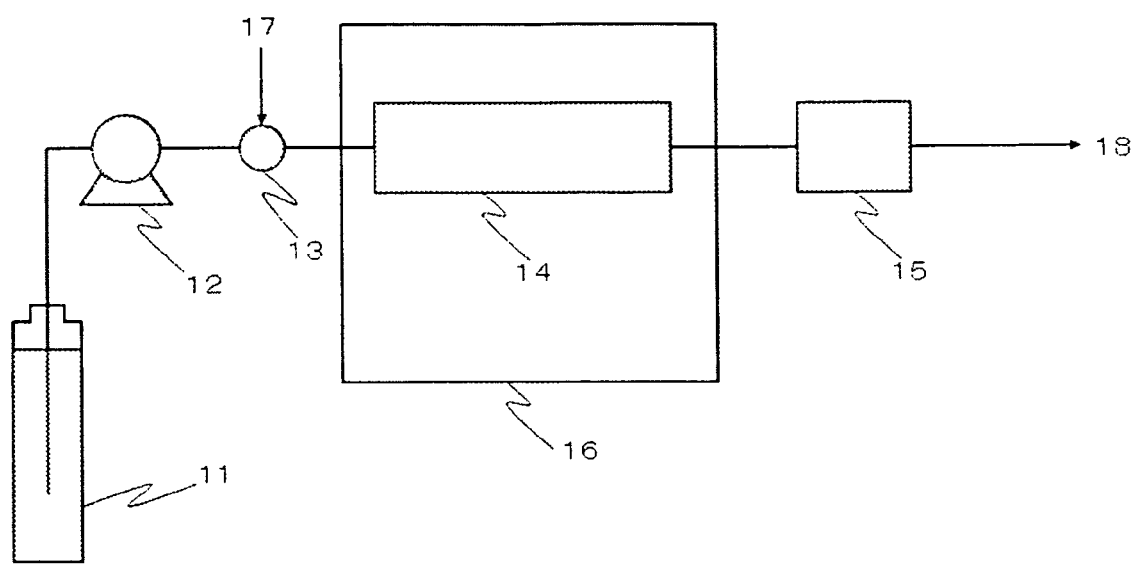
FIG. 1 shows a flow chart indicating one example of the analyzing system according to the present invention.

The method for analyzing the concentration of glue according to the present invention is based on high performance liquid chromatography (TIPLC) using a size exclusion chromatography (SEC) as a separation mechanism of solute. By Referring to FIG. 1, which is a flow chart showing one example of the analytical system according to the present invention, the principle of determining the concentration of glue is hereafter explained.

In this embodiment, a reservoir of eluent 11, a cascade pump 12, an injector 13, a separation column 14, and a detector 15 are connected through piping. First, the eluent is kept flowing at a constant flow rate from the reservoir of eluent 11 toward the separation column 14. When the baseline (background) detected by the detector is stabilized, the electrolyte solution 17 containing a minute amount of glue is injected through the injector 13. When the mixed solution of the eluent and electrolyte solution enters the separation column 14 whose temperature is kept at a constant temperature by a constant temperature bath 16, electrolyte components such as copper ion and sulfate ion are separated from glue component contained in the electrolyte solution by action of a filler in a size exclusion mode charged in the separation column 14. Namely, while a solute greater than the maximum diameter of pores in the filler (glue component in this case) is not retained in the pores in the filler, a solute smaller than the maximum diameter of pores (electrolyte component in this case) is retained in the pores in the filler. Therefore, the time required for passing through the separation column 14 is shorter for the glue component and longer for the electrolyte components. As a result, the glue component is eluted from the column and enters into the detector 15 earlier than the electrolyte components, and therefore, the peak of glue is detected earlier than that of the electrolytes by the detector 15. Accordingly, the concentration of glue in the electrolyte solution can be obtained.

The present invention, on the basis of the above-mentioned principle of analysis, enables to determine accurately and easily the concentration of glue contained in a minute amount in the electrolyte solution by employing a particularly suitable combination of the eluent and the column.

Electrolyte Solution

Electrolyte solution targeted in the present invention is not particularly restricted, provided that it contains glue. For example, the electrolyte solution containing metal ions such as copper, nickel, lead, gold, and/or manganese, and inorganic and/or organic acid(s) is targeted in the present invention. The electrolyte solution particularly targeted in the present invention is copper electrolyte solution used for production of electrolytic copper and/or electrolytic copper foil. Generally, the copper electrolyte solution primarily contains $CuSO_4 \cdot 5H_2O$ and $H_2SO_4$. Typically, it contains Cu: 40-70 g/L, $H_2SO_4$: 150-210 g/L. Occasionally, As, Sb, Bi, Ni, Te, Pb, ammonia and the like are also contained.

Further, the present invention is particularly suitable for analyzing the concentration of glue contained in a minute amount in the electrolyte solution. The concentration of glue contained in the electrolyte solution is for example 0.01-10 ppm. Typically, it is 0.1-5 ppm. More typically, it is 0.5-2 ppm.

Typically, glue primarily contains gelatin and has a molecular weight of about 500-250000. It can be produced from bone, skin, tendon, intestine and the like of non-human animal and fish by hydrolysis.

Eluent

The present invention uses, as an eluent used for a mobile phase, an aqueous solution of phosphate of alkaline metal or alkaline earth metal whose pH has been adjusted to 5 or less by adding phosphoric acid to the solution. Phosphate is used because phosphoric acid has an acid dissociation constant of 2.13 which is suitable for using as a buffer in acidic range. pH is adjusted to 5 or less by adding acid to suppress the formation of copper hydroxide. Copper generally produces hydroxide at pH 5.3 or more.

Phosphate of alkaline metal is phosphate salt of alkaline metal (Li, Na, K, Rb, Cs, or Fr). Phosphate of alkaline earth metal is phosphate salt of alkaline earth metal (Be, Mg, Ca, Sr, Ba, or Ra). Among them, for example, trisodium phosphate ($Na_3PO_4$), sodium dihydrogenphosphate ($NaH_2PO_4$), disodium hydrogenphosphate ($Na_2HPO_4$), tripotassium phosphate ($K_3PO_4$), potassium dihydrogenphosphate ($KH_2PO_4$), dipotassium hydrogenphosphate ($K_2HPO_4$), calcium phosphate ($Ca_3(PO_4)_2$), calcium dihydrogenphosphate ($Ca(H_2PO_4)_2$), calcium hydrogenphosphate ($CaHPO_4$), magnesium phosphate ($Mg_3(PO_4)_2$), magnesium dihydrogenphosphate ($Mg(H_2PO_4)_2$), magnesium hydrogenphosphate ($M_2HPO_4$) may be mentioned. Among them, phosphates of alkaline metals are preferable, and sodium dihydrogenphosphate is more preferable.

While acetic acid, citric acid and the like are mentioned as other buffers, phosphates are used in the present invention because there is a fear that carboxylic acid may interfere with the determination of glue during the analysis by an absorption spectrophotometer.

As an acid for adjusting pH, inorganic acids such as phosphoric acid, or organic acids such as acetic acid and citric acid may be mentioned. Strong acids may not be used because they have a weak buffering capacity. In the present invention, phosphoric acid is preferably used from the viewpoint of buffering capacity and whether the determination by an absorption spectrophotometer is prevented or not. Phosphoric acid includes, in addition to orthophosphoric acid, condensed phosphoric acid such as metaphosphoric acid, pyrophosphoric acid, triphosphoric acid and tetraphosphoric acid, Orthophosphoric acid is particularly preferable.

When pH of the eluent is too high, copper produces a hydroxide. However, when the pH is too low, the filler may be broken. Accordingly, pH of the eluent should be preferably adjusted to 2-4, more preferably 2-3.

Separation Column

In the present invention, a separation column having the exclusion limit molecular weight of 4000-6000 is used. The exclusion limit molecular weight means a smallest molecular weight of component which is not retained by a filler in a column. Components having a molecular weight equal to or larger than the exclusion limit molecular weight elute from the column without entering the pores of the filler On the other hand, components having a molecular weight smaller than the exclusion limit molecular weight enter the pores of the filler, resulting in the delay in eluting from the column. By this principle, the glue having a higher molecular weight is separated from the electrolyte components having a lower molecular weight. The exclusion limit molecular weight herein indicates one measured as dextran equivalent.

While a molecular weight of a molecule is not always proportioned to the size of the molecule in general, the separation of glue and the components of electrolytes can be efficiently performed, according to the results of examination by the present inventors, by using the separation column having said exclusion limit molecular weight. The exclusion limit molecular weight is preferably 4500-5500, and more preferably 5000.

As described above, glue has a molecular weight of about 500-250000 in general, and therefore, for example, when the exclusion limit molecular weight is 5000, the glue having a molecular weight smaller than 5000 can not be separated. However, an average molecular weight of glue is, generally, about 20000 prior to addition to the electrolyte solution, and glue having a molecular weight equal to or smaller than 5000 is about one sixth of total amount of glue. Accordingly, when the rapid dilution and cold storage are performed in order to reduce the degradation of glue, and the simple analysis according to the present invention is carried out, it is possible to obtain the information about the concentration of glue with an acceptable accuracy for the management of the concentration of glue in the electrolyte solution.

The filler charged into the separation column preferably has a high affinity to electrolyte components and a low affinity to glue in order to obtain a high efficiency of separation of the electrolyte components and the glue. Therefore, it is preferable to use a hydrophilic filler. As for material of the filler, any filler usually used in a separation column can be used without any particular restriction. For example, silica, carboxylated polyvinyl alcohol, polyhydroxy methacrylate, vinyl polymer and the like can be mentioned. Among them, hydrophilic vinyl polymer can be preferably used.

While the amount of filler charged into the column varies based on the type of sample, it may be exemplarily 10-20 cm$^3$ (e.g. about 14 cm$^3$). Further, while a particle diameter of the filler also can be optionally selected, considering the separation efficiency, it may be exemplarily 5-20 µm (e.g. 7 µm).

Detector

Any detector may be used without any particular restriction provided that minute amounts (e.g. 0.01-10 mg/L) of glue can be detected. For example, an absorption spectrophotometer and a differential refraction detector may be mentioned. Among them, the absorption spectrophotometer is preferable because of its high sensitivity.

When using an absorption spectrophotometer, glue can be detected at wavelength of 210 nm. The detected glue is converted into an electrical signal, and appears as a peak of voltage on a absorbance chart. The surface area of the peak, is calculated by a data processor and the concentration of glue can be thus obtained.

While any known determination method of concentration such as an absolute calibration method, a standard addition method, or an internal standard method may be used for calculating the concentration of glue, it is preferable to use the standard addition method and the internal standard method for performing a more accurate determination of the concentration because the amount of glue is minute. The standard addition method is particularly preferable for completely matching the composition of the standard sample with that of the measuring sample since the measurements may be greatly affected by the composition of the sample solution.

Conditions for Analysis

It is preferable to additionally consider the following points in performing the method for analysis according to the present invention in order to improve the accuracy of measurement.

It is preferable to inject the electrolyte solution into a high performance liquid chromatography after dilution in order to prevent the deposition of copper sulfate, since copper sulfate in the electrolyte solution is ready to deposit. Degree of dilution is not particularly restricted, provided that the deposition of copper sulfate may be prevented. The electrolyte solution is usually diluted 1-5 fold, typically 1.5-2.5 fold, e.g. 2 fold. While the dilution can be performed with water, it is preferable to use pure water so that the accuracy of measurement may not be affected.

Glue is a substance which is ready to degrade and may degrade even during the storage. In the sense of preventing the degradation of glue by sulfuric acid of high concentration, it is preferable to dilute the electrolyte solution as described above. Further, when the electrolyte solution was sampled and diluted, it is preferable to put it into cold storage at temperature equal to or below 15° C. promptly. However, when the temperature is too low, the electrolyte solution may be inconveniently frozen. It is therefore preferable to keep the temperature at 0° C. or above.

On the other hand, it is not necessary to be particularly anxious about the temperature of column and eluent because the glue is detected within 10 minutes according to the present invention and the risk of degradation of glue during the determination is low though the column is usually used at about 40° C.

As described above, the present invention enables to readily determine the concentration of glue contained in the electrolyte solution in a minute amount. Therefore, it may become easier to manage the concentration of glue in the electrolyte solution and to produce the products such as electrolytic copper and electrolytic copper foil having improved stability of quality.

EXAMPLES

Working examples are described below. However, the present inventions are not limited to these examples.

Example 1

A certain amount of copper electrolyte solution (composition: Cu: 55 g/L, $H_2SO_4$: 180 g/L, glue addition amount 1-2 mg/L) being used in an electrolytic smelting of crude copper was sampled and diluted two-fold, in situ, with pure water and was then stored in a refrigerator (5-10° C.) until the analysis is performed. The analyzing system indicated in FIG. 1 was constructed using the following devices.

<Analyzing Device>

High performance liquid chromatograph: Tosoh Corporation (HLC-8220GPC)

<Stationary Phase>

Column: Tosoh Corporation (TSKgel G2500 PW$_{XL}$)

Exclusion limit molecular weight: 5000

Filler: hydrophilic vinyl polymer (particle diameter: 7 µm)

Column size: 7.8 mm (internal diameter)×30 cm (length)

<Mobile Phase>

Eluent prepared by adding phospholic acid to 0.3 mol/L aqueous solution of sodium dihydrogenphosphate until pH of the solution becomes 2.5.

<Detector>

Tosoh Corporation an absorption spectrophotometer (type: UV-8220)

Wavelength: 210 nm

<Deta Processor>

Hardware: a personal computer commercially available from Dell K.K.

Software: a multistation GPC-8020 Model II produced by Tosoh Corporation 4 samples for determination were prepared as follows. 4 aliquots each having a volume of 25 mL were taken from the electrolyte solution. A standard sample of glue (50 mg/L) was added to each aliquot such that the concentration of glue may become 0, 1, 3 and 5 mg/L, respectively. Pure water was then added to each aliquot to prepare each sample having a volume of 50 ml. Absorbance of glue was determined for each sample according to the below-described procedure.

Figure 2:
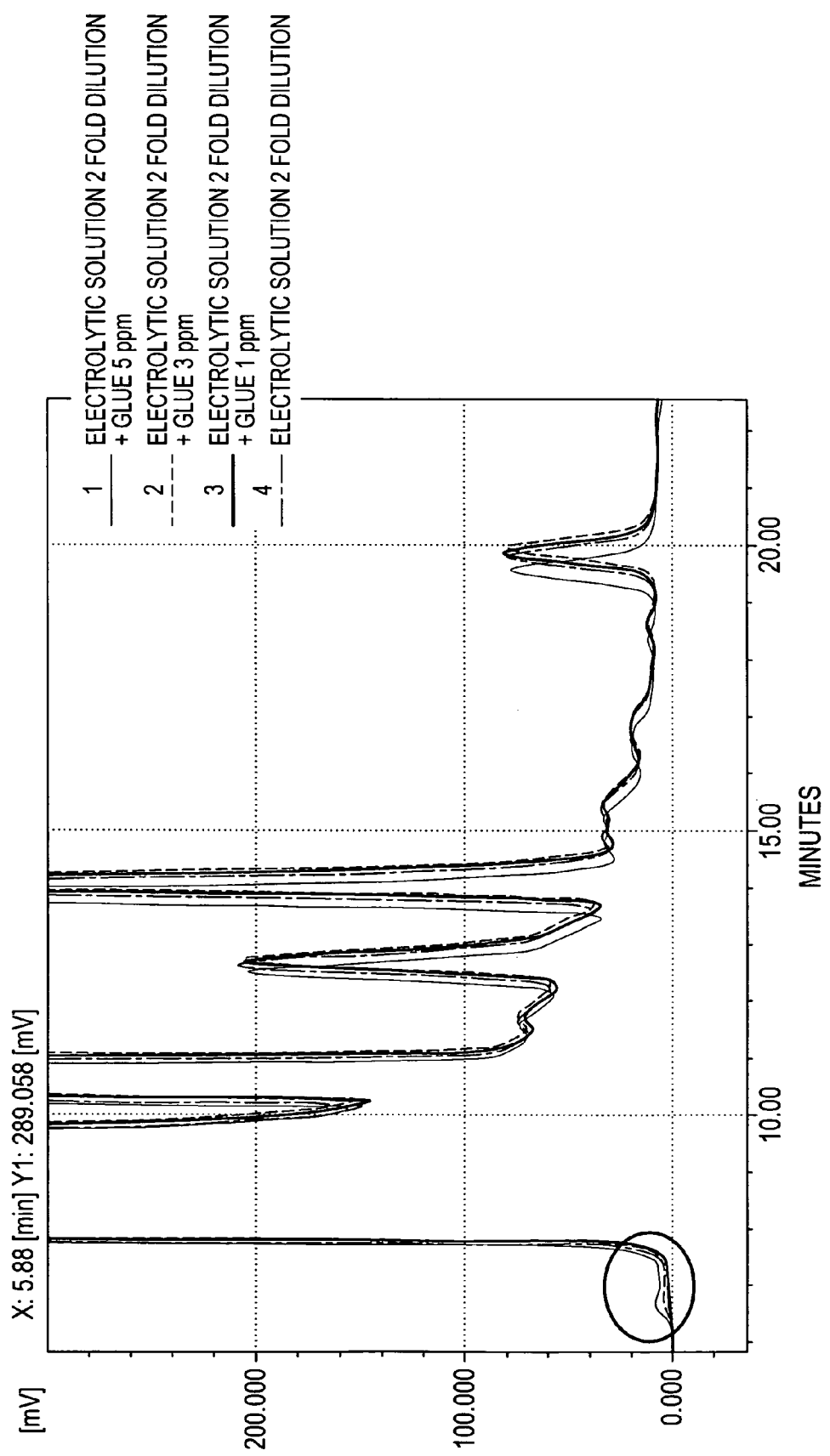
FIG. 2 shows a absorbance chart of the electrolyte solution detected in Example 1
Figure 3:
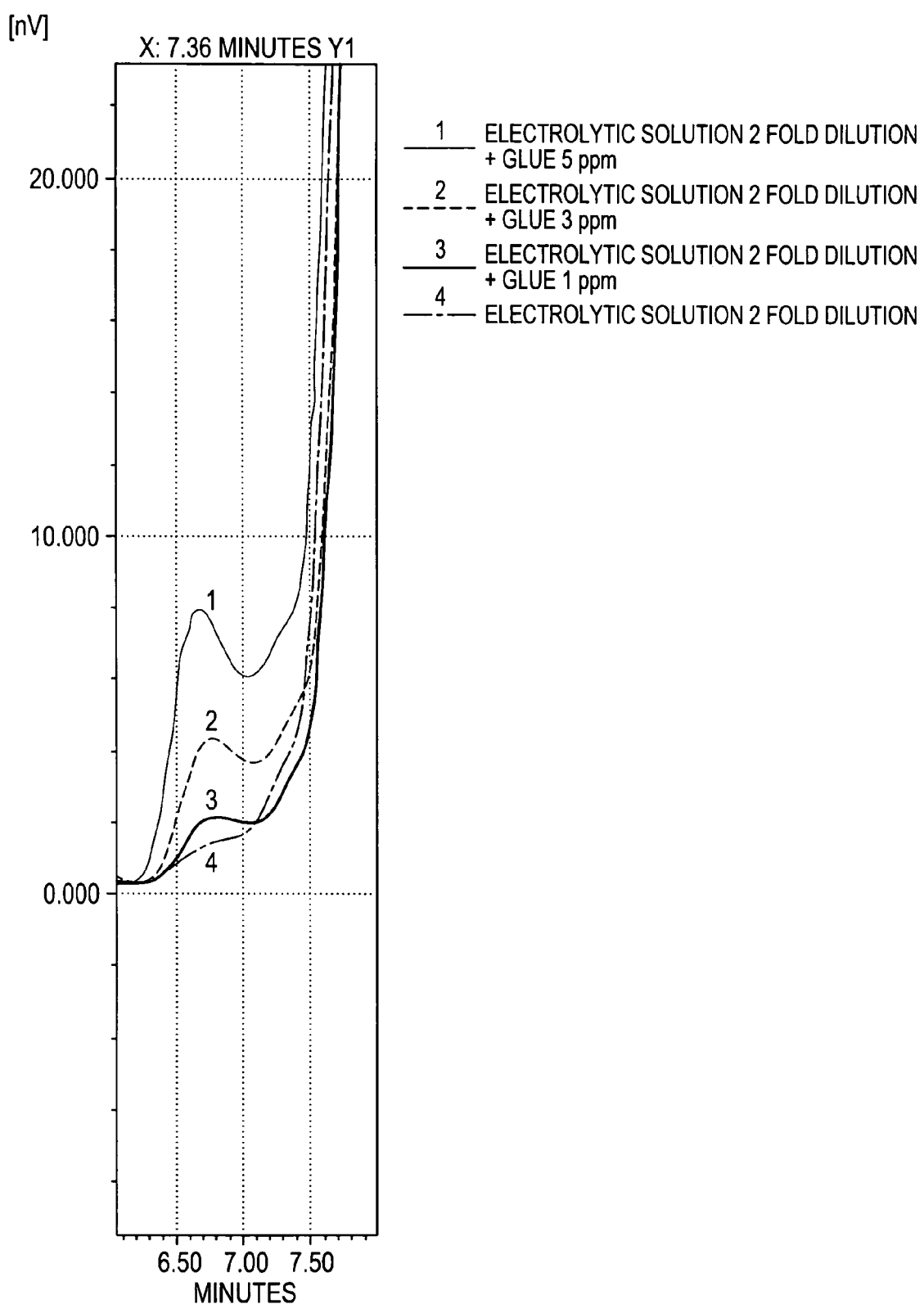
FIG. 3 shows an expanded view of a part surrounded with a circle in FIG. 2.

The column was kept at a temperature of 40° C. in a constant temperature bath. The eluent at 25° C. (room temperature) was kept flowing at a constant flow rate of 1.0 mL/min. When the baseline had been stabilized, 200 μL of sample at 5-10° C. was injected into the eluent through the injector. Subsequently, the eluent passed through the column and then a peak top of the separated and eluted glue was detected at the detector about 6.8 minutes after the injection. The absorbance chart obtained from the analysis is illustrated in FIGS. 2 and 3. FIG. 3 is a partial expanding view of FIG. 2.

The surface areas of peak of glue for the 4 samples calculated using the data processor were 4.5, 20.4, 52.3, and 84.2, respectively. Based on the result, the concentration of glue contained in the electrolyte solution was determined as 0.56 mg/L using a standard addition method. The theoretical concentration of glue in the electrolyte solution calculated from the amount of glue added to the electrolyte solution is 1-2 mg/l. Therefore, the value obtained by this determination is deemed to reflect the concentration of glue adequately, considering that the degradation of glue begins just after the addition of the glue.

Example 2

While trying to determine the concentration of glue contained in the copper electrolyte solution in the same way as described in Example 1 except that the following stationary phase was used, the separation of the electrolyte solution and glue could not be effected. It was thus impossible to determine the concentration.

<Stationary Phase>
Column: Tosoh Corporation (TSKgel G3000PW$_{XL}$)
Exclusion limit molecular weight: 20000
Filler: hydrophilic vinyl polymer (particle diameter: 7 μm)
Column size: 7.8 mm internal diameter)×30 cm (length).

The invention claimed is:

1. A method for analyzing the concentration of glue contained in a copper electrolyte solution containing an electrolyte component by using high performance liquid chromatography, consisting essentially of the steps of:

injecting the electrolyte solution into an eluent which is an aqueous mixture of sodium dihydrogenphosphate and phosphoric acid and whose pH has been adjusted to equal to or less than 5 by adding an acid to an aqueous solution of phosphate of alkaline metal or alkaline earth metal;

passing the electrolyte solution-injected eluent through a single analytical separation column having an exclusion limit molecular weight of 4000-6000 and having a particle diameter of 5-20 μm to separate the glue and the electrolyte component, the separation column including a filler of a porous hydrophilic vinyl polymer, wherein the single separation column retains the electrolyte component and allows the glue component to elute from the separation column earlier than the electrolyte components; and detecting the separated glue by a glue analyzing detector before detecting the electrolyte component, the detector performing quantitative analysis of the separated glue wherein the single analytical separation column and the detector are connected directly without an intervening column therebetween, and the glue and the electrolyte components are directly introduced to the detector, wherein the concentration of the glue is detected by the single analytical separation column and the single glue analyzing detector.

2. The method according to claim 1, wherein pH of the eluent is 2-4.

3. The method according to claim 1, wherein the electrolyte solution is diluted 1 to 5 fold with water before injected into the eluent.

4. The method according to claim 1, wherein the electrolyte solution is kept at 0-30° C. after the dilution, and then injected into the eluent in the state where said temperature condition is satisfied.

5. The method according to claim 1, wherein the glue is detected by an absorption spectrophotometer, and the concentration of glue is determined by a standard addition method.

* * * * *